United States Patent

Mascarenhas

[11] Patent Number: 5,824,467
[45] Date of Patent: Oct. 20, 1998

[54] METHODS FOR PREDICTING DRUG RESPONSE

[75] Inventor: Desmond Mascarenhas, Los Altos Hills, Calif.

[73] Assignee: Celtrix Pharmaceuticals, Santa Clara, Calif.

[21] Appl. No.: 805,808

[22] Filed: Feb. 25, 1997

[51] Int. Cl.[6] .............. C12Q 1/00; C12Q 1/54; G01N 33/53

[52] U.S. Cl. ............... 435/4; 435/14; 435/975; 530/303; 530/356; 530/350; 514/3; 514/21; 514/12; 552/502

[58] Field of Search ................ 435/4, 14, 975; 530/303, 356, 350; 514/3, 21, 12; 552/502

[56] References Cited

U.S. PATENT DOCUMENTS

| | | | |
|---|---|---|---|
| 5,187,151 | 2/1993 | Clark et al. | 435/4 |
| 5,198,340 | 3/1993 | Mukku | 435/4 |
| 5,209,920 | 5/1993 | Sternberg et al. | 435/4 |
| 5,407,913 | 4/1995 | Sommer et al. | 514/21 |
| 5,444,047 | 8/1995 | DiPasquale | 435/4 |

*Primary Examiner*—Louise N. Leary
*Attorney, Agent, or Firm*—Morrison & Foerster LLP

[57] ABSTRACT

Methods are provided for formulating models for predicting whether subjects will respond to a particular drug or treatment regimen. Biochemical profiles are obtained (by measuring a variety or biochemical parameters) for a test group before and after treatment with the drug or regimen. These values are used formulate a specific predictive method for the particular drug or treatment regimen. The predictive measurement is then used with biochemical parameters obtained from a subject to predict whether that subject will respond to the particular drug or treatment regimen.

6 Claims, 6 Drawing Sheets

METHODS FOR PREDICTING DRUG RESPONSE

TECHNICAL FIELD OF THE INVENTION

This invention relates to methods for predicting the responsiveness of a subject to a particular drug or treatment regimen.

BACKGROUND OF THE INVENTION

The variability of individual responses to drugs can complicate the treatment of many disorders. Even within a population that is relatively homogenous (i.e., same sex, a narrow range of ages, etc.), some subjects will respond well to a particular drug, while other subjects will respond poorly.

The problem of interpatient variability is particularly serious among sufferers of chronic diseases. For example, many drugs utilized to treat chronic psychological disorders (e.g., depression) require many days or even weeks before an effect, if any, is seen. For subjects that do not respond to the drug, the "wait and see" period only prolongs the period of suffering.

U.S. Pat. No. 5,209,920 discloses a method for predicting susceptibility to inflammatory diseases. The method disclosed involves administering a test compound which is known to affect the hypothalamic-pituitary-adrenal axis, then measuring the levels of pituitary and adrenal hormones. Individuals that do not respond to the test compound with increased pituitary and adrenal hormones are deemed "susceptible." This disclosure does not provide any teaching regarding a method for predicting whether a subject will respond to a particular drug or treatment regimen.

Accordingly, there is a need in the art for a method of predicting the responsiveness of a subject to a particular drug or treatment regimen. A method for predicting responsiveness would allow physicians and other medical professionals to quickly determine an effective drug or treatment regimen for a particular subject, thus reducing the subject's suffering and expense. A method for predicting responsiveness would also reduce or eliminate a subject's exposure to drugs or treatment regimens that are not effective, thereby reducing or eliminating suffering from side effects of such ineffective drugs or treatment regimens.

DETAILED DESCRIPTION OF THE INVENTION

It is an object of the invention to provide methods for formulating predictive models of subjects' responsiveness to a drug or treatment regimen.

It is a further object of this invention to provide methods for predicting a subject's responsiveness to a drug or treatment regimen. It is yet a further object of the instant invention to provide methods for predicting a subject's responsiveness to a administration of recombinant human insulin-like growth factor I (rhIGF-I) or IGF-I complexed with insulin-like growth factor binding protein 3 (IGFBP-3).

It is a further object of the instant invention to provide methods and diagnostic kits for predicting a subject's responsiveness to a drug or treatment regimen.

BRIEF DESCRIPTION OF THE DRAWINGS

FIG. 1 shows a correlation density plot for biochemical parameters from clinical trial 9602. Bold face indicates responses that are statistically significant. Abbreviations used: "nd" means not determined; "IGF-I" means insulin-like growth factor I; "IGF-I" means insulin-like growth factor II; "IGFBP-2" means insulin-like growth factor binding protein 2; "IGFBP-3" means insulin-like growth factor binding protein 3; "LH" means leutinizing hormone; "EPO" means erythropoietin; "C1CP" means procollagen peptide; "PTH" means parathyroid hormone; "BSAP" means bone specific alkaline phosphatase; "A4" means androstenedione; "DHEA-S" means dehydroepiandrosterone sulfate; "T3" means triiodothyronine; "T4" means tetraiodothyronine; "CBG" means cortisol binding globulin; and "SHBG" means steroid hormone binding globulin.

FIG. 3 shows correlations between biochemical responses to administration of IGF-I/IGFBP-3 complex. Panel A shows IGF-I response versus IGFBP-3 response. Panel B shows estradiol response versus IGF-I response. Panel C shows estradiol response versus C1 CP response.

MODES OF CARRYING OUT THE INVENTION

The invention relates to methods for predicting a subject's response to a particular drug or treatment regimen. A subject's biochemical profile (e.g., serum concentrations of thyroid, adrenal, gonadal and pituitary hormones, organ-specific markers and the like) is measured prior to treatment and used to predict the subject's response to a particular drug or treatment regimen.

The invention also relates to methods for formulating predictive models for responsiveness to a particular drug or treatment regimen. A predictive method may be created for any particular drug or treatment regimen. The method for formulating predictive models involves:

(a) selecting a cohort of test subjects;

(b) obtaining an biochemical profile from each of the test subjects by measuring various biochemical parameters;

(c) administering a particular drug or treatment regimen;

(d) measuring the effects of the drug or treatment regimen;

(e) performing correlation tests between the biochemical parameters and the effects of the drug or treatment regimen;

(f) selecting biochemical parameters that correlate with the effects of the drug or treatment regimen; and (g) deriving a predictive method between the selected biochemical parameters and the response to the drug or treatment regimen.

Not all subjects respond identically to any given drug or treatment regimen. For most, if not all drug and treatment regimens, subjects respond in varying degrees, and some percentage of the subjects fail to respond entirely. A method for formulating a predictive model that can predict a particular subject's response to a particular drug or treatment regimen has been discovered. A method for predicting a particular subject's response to a particular drug or treatment regimen has also been discovered. Also included within the instant invention are diagnostic kits utilizing a predictive method created in accordance with the invention.

Different subjects diagnosed with a given disorder generally exhibit widely varying biochemical profiles. The response of an individual to a drug is dependent on that individual's neuroendocrine status that, in turn, is reported by some aspect of the individual's biochemical profile. However, because the interactions between the different biochemical and endocrine sub-systems (e.g., between the somatotropic, thyroid and adrenal axes) are extremely complex, it is necessary to look at a large number of biochemical markers before devising a predictive method. The methods of the invention, therefore, utilize a broad biochemical profile to predict whether a given subject will respond to a particular drug or treatment regimen.

The methods within the instant invention are not based on intuitive logic but rather are based on analyzing the effect of a drug or treatment regimen on known biochemical and/or endocrine elements.

The formulation of a predictive model for the prediction of a subject's procollagen peptide (C1CP) response to treatment with a complex of recombinant human insulin-like growth factor I (rhIGF-I) and recombinant human insulin-like growth factor binding protein 3 (rhIGFBP-3) is exemplified herein. The method of formulating a predictive model for predicting response to rhIGF-I and rhIGFBP-3 complex (rhIGF/IGFBP-3) can be applied to formulate a method for predicting the response of the rhIGF-I/rhIGFBP-3 complex in osteoporotic subjects. The method of formulating a predictive model is also applicable to any other drug or treatment regimen, such as antidepressant medications (e.g., fluoxetine), anti-ulcer medications, medications acting on the cardiovascular system (e.g., anti-hypertensive medications), and the like.

In the method for formulating a predictive model for predicting a subject's response, a cohort is selected by criteria known to one of skill in the art. Preferably, the cohort is approximately representative of the population for which the drug or treatment regimen is intended.

A biochemical profile is determined by measuring serum levels of various biochemical molecules and other serum markers. A biochemical profile should include measurements of biochemical molecules and serum markers from a wide variety of endocrine and metabolic systems. Preferably, a biochemical profile will include measurements of biochemical parameters selected from a wide variety of endocrine systems, including, but not limited to, the somatotropic axis (e.g., IGF-I, IGF-II, IGFBP-3, growth hormone (GH) and the like), the thyroid axis (triiodothyronine (T3), tetraiodothyronine (T4), thyroid stimulating hormone (TSH), thyroglobulin, and the like), the adrenal axis (dehydroepiandrosterone(DHEA), dehydroepiandrosterone-sulfate (DHEAS), cortisol, aldosterone, and the like), the gonadal axis (testosterone, androstenedione, estradiol, and the like), and the hypothalamic-pituitary axis (prolactin (PRL), leutinizing hormone (LH) and the like). A biochemical profile may also optionally include serum levels of markers specific to certain processes or organ systems, including parameters including, but not limited to, levels of anabolic markers (such as procollagen peptide (C1CP) and the like), bone markers (such as osteocalcin, bone alkaline phosphatase, and the like) and renal hormones (such as renin, angiotensin, and the like).

Administration of the test drug or treatment regimen may begin following acquisition of samples sufficient to perform all testing necessary to establish a biochemical profile for each member of the test cohort. The drug or treatment regimen may be administered to the test cohort in any manner that is known in the art; the exact method of administration, dose level and dosing schedule will be specific to the particular drug or treatment regimen, as will be apparent to one of skill in the art.

During the administration of the drug or treatment regimen, or subsequent to the administration (depending on the particular drug or treatment regimen and the response that is to be measured), responsiveness is measured. As with the exact treatment details, the measurement of responsiveness will be specific to the particular drug or treatment regimen, as will be apparent to the skilled artisan. In the case of IGF or IGF/IGFBP-3 complex, responsiveness may be measured by testing bone markers (e.g., bone mineral density, serum levels of osteocalcin, bone alkaline phosphatase and the like.), renal markers (e.g., serum levels of renin, creatinine clearance, and the like), anabolic markers (such as serum levels of C1CP, nitrogen balance, lean body mass and the like), wound healing indices (such as wound closure rates and the like), psychological indices (such as improvement in cognitive or memory skills, improvement in symptoms of psychological disorders and the like), or any other indicator of responsiveness, as will be apparent to one of skill in the art. Measures of responsiveness are preferably normalized to a baseline level. The data set of the measures of responsiveness is referred to as the "efficacy set."

After a biochemical profile has been established and measures of responsiveness have been obtained for the members of the test cohort, the individual parameters of the biochemical profile are tested for correlation with the measures of responsiveness. Correlation testing may be done using any valid statistical testing method known to the art.

Biochemical parameters that correlate well (either positively or negatively) are selected for use in deriving the predictive method. It is preferable to begin investigating the three or four biochemical parameters with the highest r values. Preferably, biochemical parameters that correlate with an r value of greater than 0.4 are selected for use in deriving the predictive method. The selected biochemical parameters are then combined to derive the predictive method. In generating a predictive method, operations such as addition, subtraction, product, ratio, and the like should be performed between each pair of the selected data sets (and derivative sets representing square root, logarithm, and the like) of each should be examined, in each case comparing the resulting transformed data set with the efficacy set. Those comparisons yielding progressively higher "r" values are retained for further combinations, until the best possible predictive method is generated. The value of each biochemical parameter selected for use in deriving the predictive method may also be multiplied, divided, added to, or subtracted from when deriving the predictive relationship, in order to make maximize the accuracy of the predictive method. The values of each biochemical parameter selected for use in deriving the predictive method may be further modified by any standard mathematical operation, such as raising to a power, taking a logarithm, finding a root, and the like, in order to maximize the accuracy of the predictive method.

The specific predictive method derived by the method for formulating a predictive model may then be utilized to predict the responsiveness of a subject to a particular drug or treatment regimen. The particular biochemical values that are utilized in the predictive method are measured in the subject, then employed in the predictive method. As shown in Example 1, serum levels of TSH, total T4, and IGF-I are used to create a predictive method to determine the effect on a subject's C1CP and/or IGFBP-3 blood levels of the administration of IGF/IGFBP-3 complex. A physician or other skilled artisan may then utilize this predicted response value to decide whether or not to treat the subject with IGF/IGFBP-3 complex in order to increase the subject's C1CP and/or IGFBP-3 levels. This predicted response to IGF/IGFBP-3 complex administration will be useful in deciding whether to treat a subject in need of an anabolic treatment, particularly an anabolic treatment that improves bone, muscle and/or connective tissue strength.

The predictive methods formulated by the methods for formulating specific predictive methods may also be used to provide diagnostic kits. A diagnostic kit based on a predictive method formulated in accordance with methods of the invention includes reagents for measuring the biochemical parameters that are utilized in the predictive method. Reagents for measuring biochemical parameters are well known in the art, and may include enzyme-linked immunosorbent assays (ELISA), radioimmunoassays (RIA), and any other assays known in the art for specific detection of the level of a particular biochemical parameter. Such a diagnostic kit also optionally includes instructions, software, and/or a worksheet for calculating the predicted responsiveness, based on the particular biochemical parameters tested.

Instructions for the kit include a listing of required materials and assay results, a mathematical representation of the predictive relationship, and a protocol for utilizing the biochemical parameter(s) with the mathematical representation to produce a predicted responsiveness. Software included with the kit operates on a digital computer, prompts the user for the necessary biochemical parameters, and, using the predictive method, calculates and returns the predictive responsiveness. A worksheet for the kit includes a mathematical representation of the predictive method, and allows the user to calculate the predicted responsiveness based on the biochemical parameters obtained using the assays in the kit.

EXAMPLES

Example 1

Data sets from two separate clinical trials of rhIGF-I/IGFBP-3 complex were utilized to create a predictive method for response to the complex. The first study ("9602") involved repeated intravenous administration of rhIGF-I/IGFBP-3 to normal volunteers (male and female), ages 20–53. The second trial ("9604") involved continuous subcutaneous infusion of rhIGF-I/IGFBP-3 complex to normal female volunteers, ages 55–70.

Biochemical profiles were determined for each test subject by assaying serum levels of biochemical parameters. The effects of inter-subject variability on the analysis was minimized by calculating the biochemical response of each subject on a relative basis. For each biochemical marker, the level at the end of the study was compared with that at the beginning, then expressed as a percentage of baseline. Statistical methods, including measures of significance were applied to these data sets.

The relative IGF-responsiveness of each subject (with respect to each of the biochemical markers, especially IGF-I, IGF-II, IGFBP-2, IGFBP-3, DHEAS, androstenedione, estradiol, total T4, and procollagen peptide (C1CP)) was then computed by comparison with the mean for each treatment group. These data sets are shown in Table 1 (9602) and Table 2 (9604).

TABLE 1

| SUBJECTS | IGF-I resp | IGF-II resp | BP-2 resp | BP-3 resp | C1CP resp | Osteo resp | BSAP resp | EPO resp | A.Renin res | LH resp | SHBG re | PRL resp |
|---|---|---|---|---|---|---|---|---|---|---|---|---|
| 2 | 88.7 | 103 | 101 | 93.7 | 89 | 65 | 113.1 | 111.8 | 61 | 187.8 | 100 | 111.9 |
| 3 | 102 | 88.1 | 115 | 86.5 | 107 | 187.5 | 87.9 | 78.6 | 70.7 | 63.4 | 101.1 | 67.3 |
| 4 | 119.3 | 100 | 112 | 124.3 | 107 | 68.1 | 100.9 | 82.7 | 74.8 | 28.1 | 106.7 | 122.8 |
| 6 | 90.7 | 110.5 | 73 | 96.4 | 97 | 78.8 | 96.3 | 126.8 | 194.3 | 122 | 91 | 99 |
| 7 | 109.8 | 89.7 | 64 | 94.5 | 105 | 94.4 | 101 | 98 | 94.6 | 62.2 | 99 | 108.1 |
| 8 | 70.7 | 94.8 | 94 | 95.6 | 87 | 54.2 | 101.9 | 60.4 | 47.9 | 205.8 | 120.8 | 109.9 |
| 11 | 125.6 | 98.3 | 103 | 109.9 | 116 | 112.5 | 88.5 | 81.7 | 129.2 | 72.3 | 90.1 | 90.1 |
| 12 | 92.9 | 113.8 | 141 | 100 | 92 | 136.1 | 106.7 | 159.9 | 113.9 | 116 | 89.1 | 92.8 |
| 14 | 91.6 | 104.8 | 177 | 84.7 | 104 | 100.8 | 109 | 100 | 85.3 | 112 | 104.7 | 66.7 |
| 15 | 92.1 | 111.9 | 30 | 124.2 | 113 | 96 | 93 | 93.5 | 125.7 | 88 | 70.1 | 124.3 |
| 16 | 115.8 | 83.3 | 93 | 90.3 | 83 | 102.4 | 98 | 107.2 | 89.9 | n.d. | 126 | 112.3 |

| SUBJECTS | tT4 resp | FT4resp | TG resp | TBG resp | tT3 resp | DHEAS re | DHEA res | A4 resp | Testost re | CBG resp | Cort resp | Estrad resp |
|---|---|---|---|---|---|---|---|---|---|---|---|---|
| 2 | 98 | 97.8 | 117.6 | 100 | 101.2 | 90 | 87.1 | 205 | 98.9 | 97.9 | 79.1 | 77.7 |
| 3 | 115 | 121.5 | 108.4 | 80.2 | 90.7 | 113 | 68.3 | 52 | 105.6 | 108.3 | 53.3 | 55.3 |
| 4 | 97 | 107.5 | 98.3 | 126.4 | 109.3 | 106 | 136.6 | 71 | 98.9 | 104.2 | 139.1 | 86.6 |
| 6 | 88 | 74.2 | 80.7 | 93.4 | 98.8 | 91 | 10S.9 | 76 | 94.4 | 89.6 | 127.6 | 181 |
| 7 | 97 | 119.6 | 129.6 | 117.4 | 102.2 | 102 | 94.5 | 109 | 124.4 | 112.9 | 129.2 | 131.5 |
| 8 | 88 | 98 | 84.3 | 86.2 | 94.6 | 102 | 95.6 | 65 | 118.9 | 99 | 97.9 | 77.8 |
| 11 | 101 | 93.1 | 75.7 | 88.1 | 106.5 | 82 | 109.9 | 65 | 64.5 | 95 | 74 | 62 |
| 12 | 113 | 88.2 | 110.4 | 108.3 | 95.7 | 113 | 100 | 157 | 129.9 | 93.1 | 100 | 129.6 |
| 14 | 87 | 108 | 84.8 | 140.1 | 108.1 | 99 | 84.7 | 109 | 82.5 | 96.2 | 91.4 | 95.6 |
| 15 | 92 | 100.9 | 84.8 | 79 | 102 | 100 | 124.2 | 78 | 99 | 88.5 | 97.4 | 111.5 |
| 16 | 119 | 91.2 | 130.4 | 81.5 | 89.9 | 101 | 90.3 | 117 | 118.6 | 114.4 | 110.3 | 92.9 |

TABLE 2

| SUBJECTS | EPO resp | tT4 resp | TG resp | tT3 resp | IGF-II resp | IGF-I resp | IGFBP3 re | ClCP resp | LH resp | PRL resp | IGFBP-1 re | IGFBP-2 resp |
|---|---|---|---|---|---|---|---|---|---|---|---|---|
| 5 | 107.5 | 103.5 | 73.1 | 129.6 | 89.7 | 138.3 | 122.7 | 82.9 | 89 | 52.8 | 132 | 146.2 |
| 6 | 107.9 | 92.2 | 10.2.1 | 90.1 | 138.7 | 83.3 | 95.5 | 109.8 | 106.9 | 128 | 93.3 | 67.8 |
| 7 | 84.5 | 104.3 | 124.8 | 80.4 | 71.7 | 78.5 | 81.7 | 107.3 | 104.1 | 119.1 | 74.8 | 86 |
| 109 | 112 | 89.2 | 99.1 | 106.9 | 72.8 | 113.1 | 97.7 | 79.2 | 78.7 | 99.8 | 117.4 | 79.6 |
| 110 | 75.7 | 111.9 | 74.3 | 93.8 | 90.9 | 115.9 | 109.6 | 146.8 | 122.1 | 86.2 | 73.4 | 111 |
| 112 | 112.3 | 99.1 | 126.5 | 99.3 | 136.1 | 71 | 92.7 | 80.4 | 99.3 | 114.2 | 109.2 | 79.6 |
| 201 | 63.4 | 106.2 | 19.1 | 101.4 | 130.6 | 90.9 | 80.8 | 86.4 | 111 | 140.8 | 64.5 | 111.5 |
| 203 | 187.7 | 91.7 | 143.8 | 106.7 | 56.6 | 153.3 | 132.4 | 146.8 | 112.4 | 60.8 | 110.1 | 185.9 |
| 204 | 48.9 | 102 | 137.2 | 92 | 112.9 | 55.8 | 86.0 | 70 | 76.6 | 98.5 | 125.4 | 43.3 |

| SUBJECTS | IGF-II resp | PRL resp | Estradiol re | EPO resp | Osteocal re | ClCP resp | BSAP resp | Osteocal re | Cortisol | DHEAS re | Testostre | A4 resp | tPTH resp |
|---|---|---|---|---|---|---|---|---|---|---|---|---|---|
| 5 | 89.7 | 52.8 | 108.7 | 107.5 | 81.6 | 82.9 | 101.6 | 81.6 | 59.8 | 88.2 | 63.1 | 36.2 | 82.6 |
| 6 | 138.7 | 128 | 86 | 107.9 | 116.9 | 109.8 | 101.6 | 116.9 | 9I | 93 | 97.6 | 84 | 108.9 |
| 7 | 71.7 | 119.1 | 105.4 | 84.5 | 101.5 | 107.3 | 96.7 | 101.5 | 149.3 | 118.8 | 139.4 | 179.9 | 108.6 |
| 109 | 72.8 | 99.8 | 101.5 | 112 | 166.4 | 72.9 | 128.8 | 166.4 | 92.1 | 128.3 | 131.3 | 190.6 | 135.8 |
| 110 | 90.9 | 86.2 | 129.6 | 75.7 | 74.9 | 146.8 | 83.7 | 74.9 | 114.8 | 79.9 | 93 | 57.9 | 73.3 |
| 112 | 136.1 | 114.2 | 68.7 | 112.3 | 58.7 | 80.4 | 87.5 | 58.7 | 93.1 | 91.7 | 75.6 | 51.6 | 91 |
| 201 | 130.6 | 140.8 | 81.7 | 63.4 | 32.8 | 86.4 | 117.4 | 32.8 | 59.5 | 112.5 | 137.1 | 119.5 | 138.4 |
| 203 | 56.6 | 60.8 | 150.9 | 187.7 | 202.8 | 146.7 | 97.1 | 202.8 | 45.7 | 77.6 | 90.5 | 76.9 | 110.9 |
| 204 | 112.9 | 98.5 | 67.5 | 48.9 | 64.4 | 70 | 85.6 | 64.4 | 194.8 | 109.9 | 72.5 | 103.7 | 50.7 |

Figure 1:
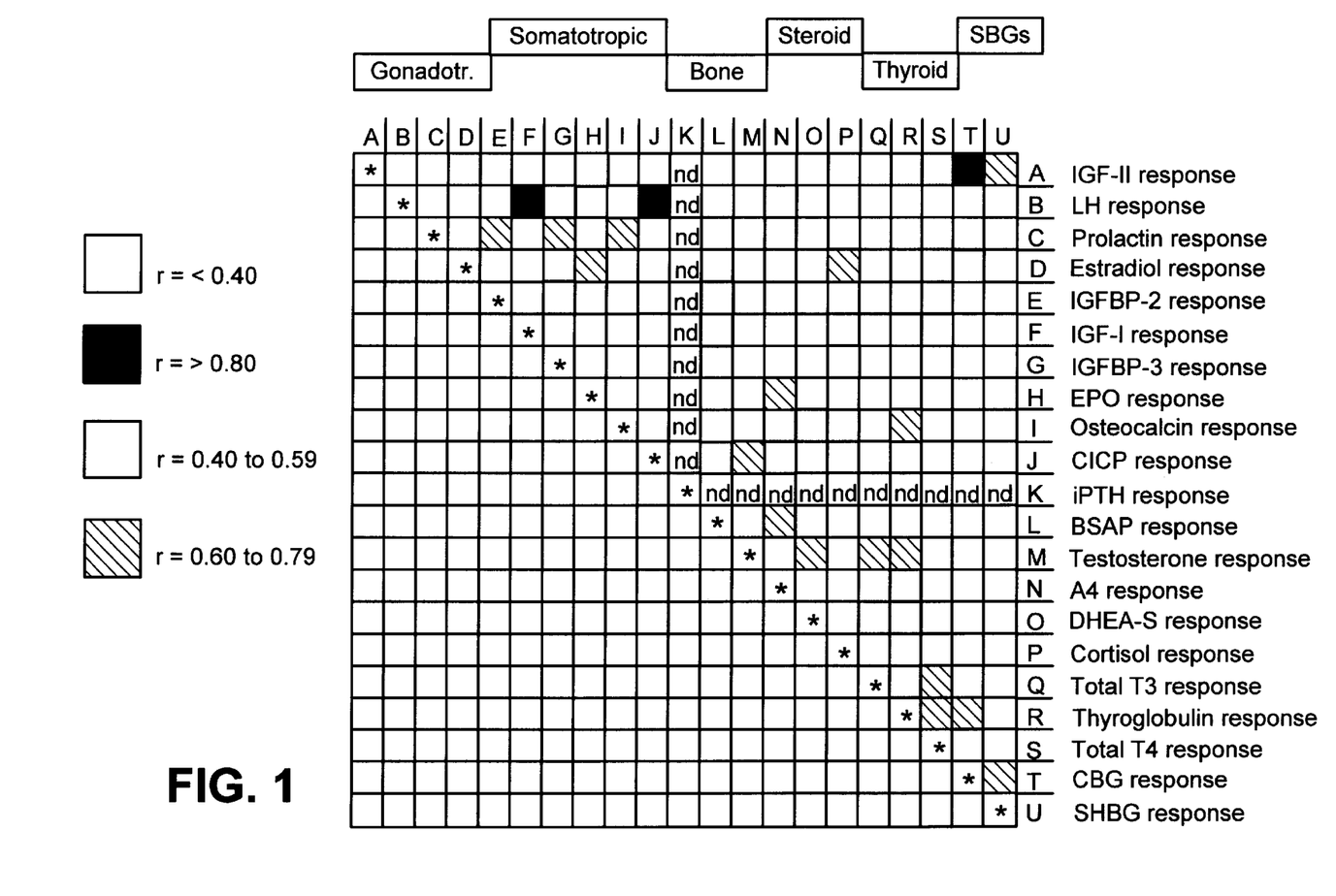
Figure 2:
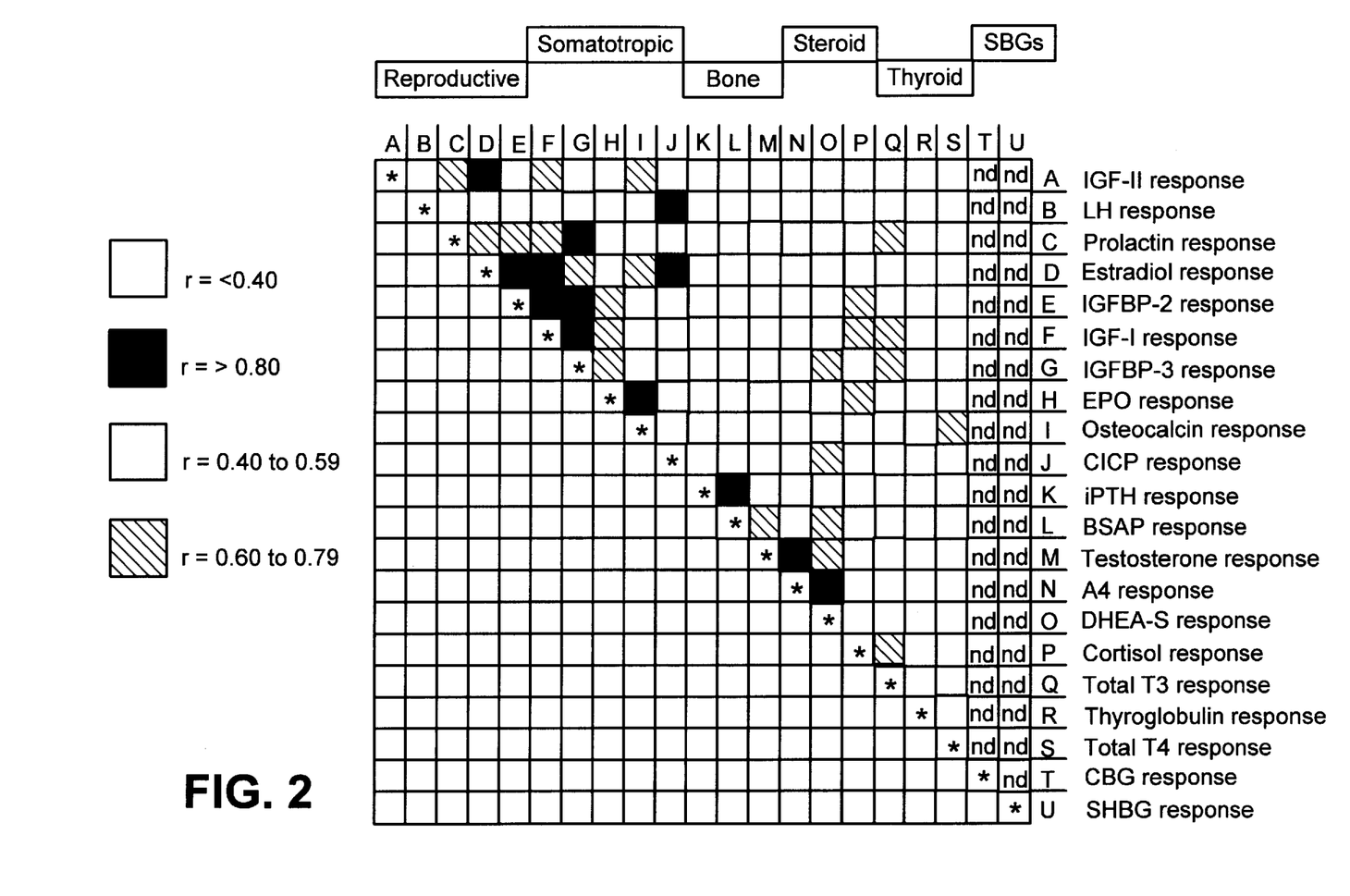
FIG. 2 shows a correlation density plot for biochemical parameters from clinical trial 9604. Bold face indicates responses that are statistically significant. Abbreviations are the same as in FIG. 1.

The data sets containing each subject's responsiveness to IGF-I/IGFBP-3 complex were then compared pairwise by calculating coefficients of correlation between the data sets. A density map of these correlations is shown in FIG. 1 for 9602 and FIG. 2 for 9604. Inspection of the density maps reveals a significant non-randomness to the distributions of density for each study. Correlations are observed to endocrine responsiveness within functional areas (somatotropic, adrenal, thyroid), suggesting that these kinds of statistical computations are valid and meaningful. Further, this method of representing endocrine responsiveness is novel and provides insights into the inter-connectivity between endocrine sub-systems.

Figure 3A:
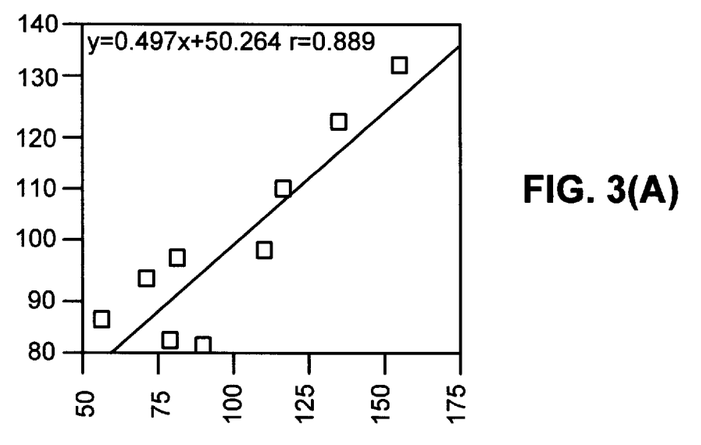
Figure 3B:
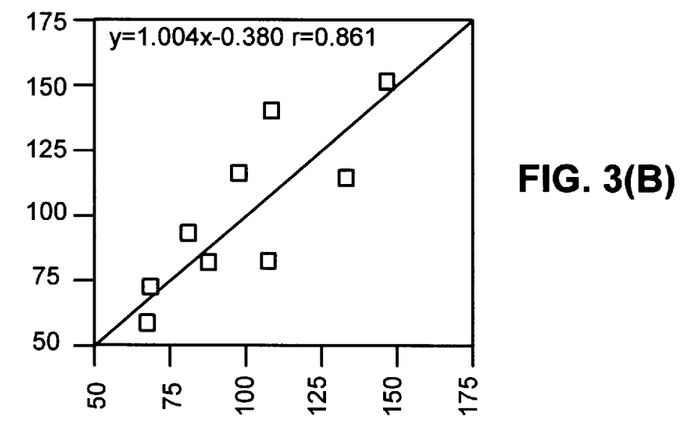
Figure 3C:
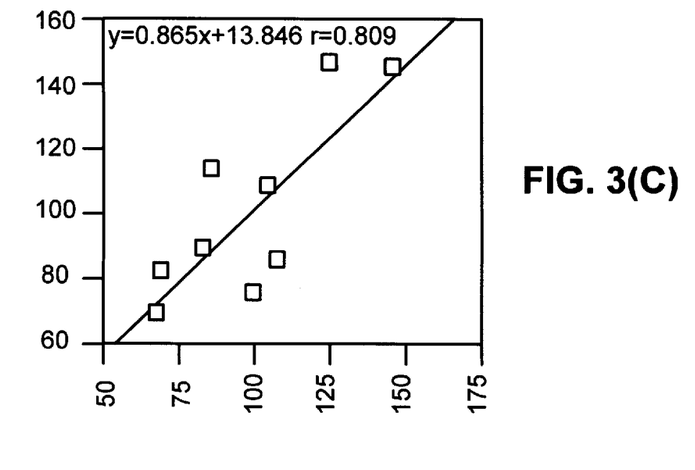

The correlation between the responsiveness to three biochemical markers (IGF-I, IGFBP-3 and estradiol) is graphically represented in panels A–C of FIG. 3. These graphs show that each subject appears to respond in a coordinate manner with respect to each of these biochemical indices. Similar connections were observed for other high density areas on the correlation maps.

In order to compute "effectiveness," the areas of density of the map with the highest interconnectiveness were chosen for further investigation. The somatotropic and bone group of biochemical markers, including C1CP, IGF-I, IGF-II, IGFBP-2, IGFBP-3, estradiol and erythropoietin (EPO) were chosen. For simplicity, a formula based on only the C1CP and IGFBP-3 responses was derived.

The working definition of drug efficacy for this example was the average of the data sets for the responses to C1CP and IGFBP-3 ("efficacy set"). Basal levels of various biochemical markers in the population in each study prior to receiving drug were compared in pairwise fashion with the efficacy set. All of those biochemical markers whose sets correlated (positively or negatively) with an "r" value exceeding 0.4 were further investigated for inclusion as factors in a predictive relationship.

The data sets for basal levels of IGF-I, total T4 (tT4) and TSH were selected for further study. By empirical derivation using the procedure outlined above, the following formula (Formula #1) was derived:

$$P = \frac{\log([TSH]+1) X [tT4]}{[IGF-1]}$$

where,

P is the predicted efficacy of the drug

[TSH] is the basal concentration of TSH ($\mu$IU/mL)

[tT4] is the basal concentration of total T4 (ng/mL)

[IGF-I] is the basal concentration of IGF-I (ng/mL).

The values utilized in this predictive method should lie within the normal clinical range. Any major derangement in a particular endocrine axis may prejudice the value of that biochemical marker in a predictive method. For the above factors, the normal clinical ranges are:

TSH: ca. 0.5–5.0 $\mu$IU/mL.

tT4: ca. 40–130 ng/mL.

IGF-I: ca. 70–440 ng/mL.

If a subject's value lies just outside the normal range for one of these factors, the closest boundary value within the normal range should be used in the computation.

Figure 4:
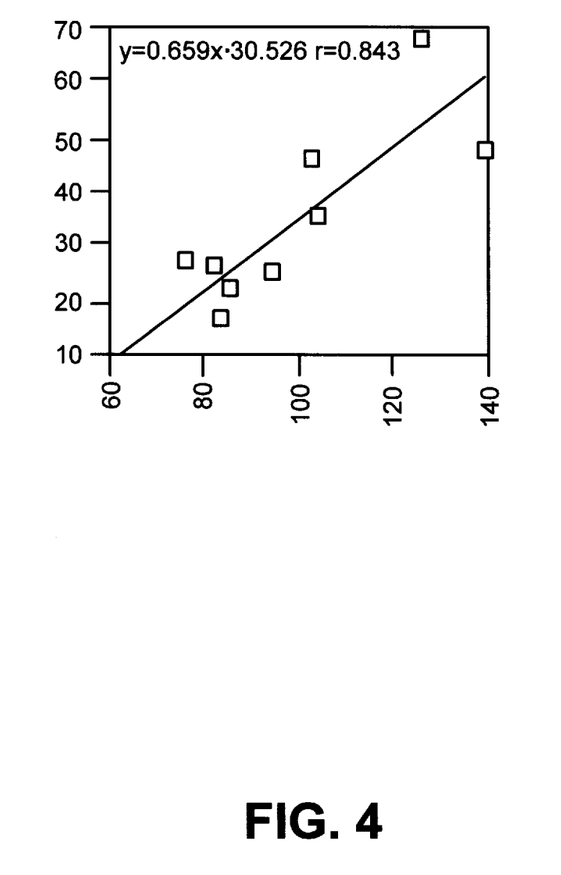
FIG. 4 shows a crude predictive relationship plotted using data from 9602 clinical trial data. The predictive method used was the product of the log[TSH] and total T4.
Figure 6:
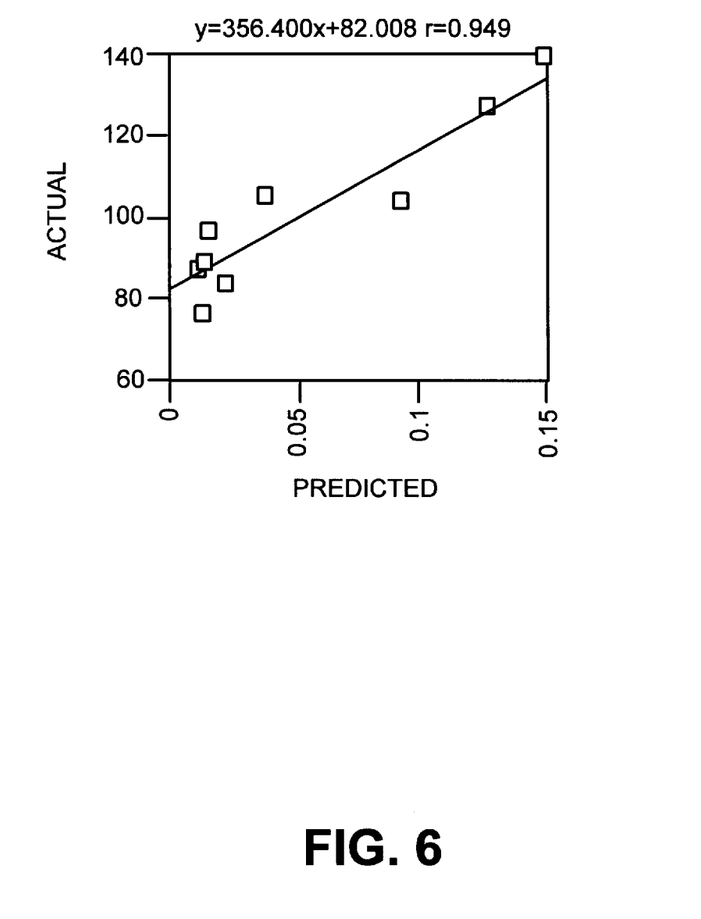
FIG. 6 is a plot of predicted versus actual responses using 9604 clinical trial data. The predictive method used is exemplified in Example 1.

FIGS. 4 and 6 show part of the derivation of the above formula. In FIG. 3, only the TSH and tT4 values were utilized in the computation, leading to an "r" value of 0.843. This value was raised to 0.949 by including the [IGF-I] value in the computation.

Figure 5:
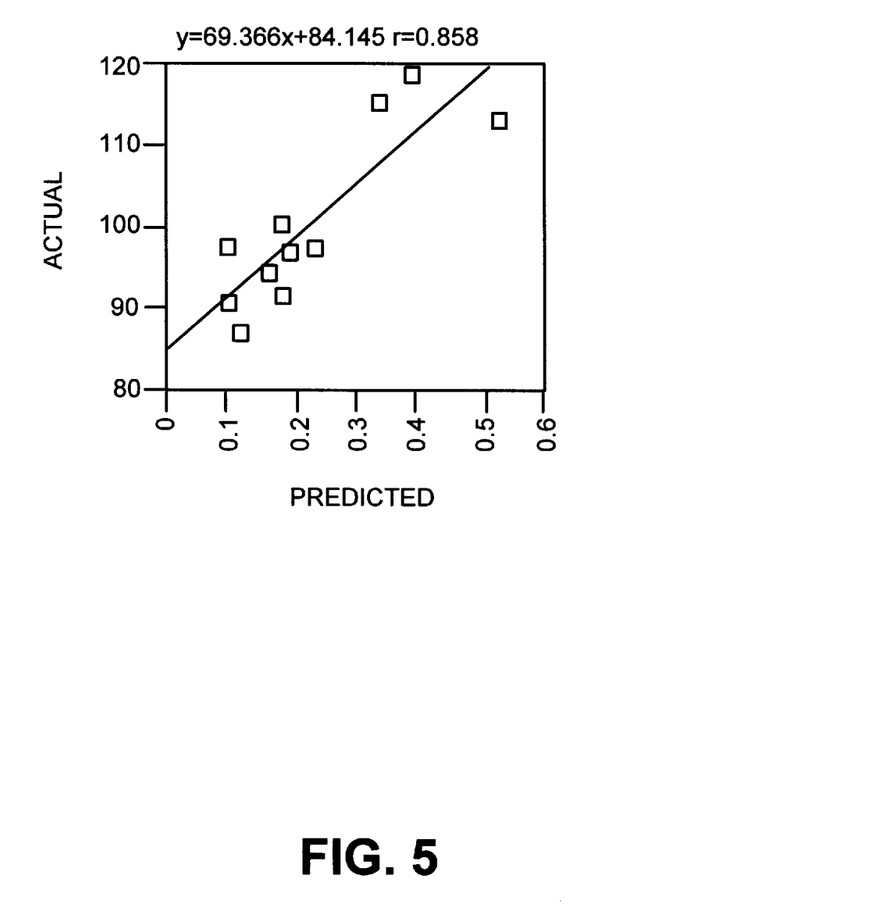
FIG. 5 shows a plot of predicted versus actual responses using 9602 clinical trial data. The predictive method used is shown in Example 1.

The generality of this particular predictive method is shown by applying it to the data set from 9602. Despite vast differences in the populations used in the two studies (i.e., age and gender), and in the mode of drug administration, the predictive method of Formula #1 fits the data set of 9602 extremely well (FIG. 5). It should also be mentioned that this predictive method can be used to predict either C1CP or IGFBP-3 responsiveness individually.

The patents, patent applications, and publications cited throughout the disclosure are incorporated by reference herein in their entirety.

The present invention has been detailed both by direct description and by example. Equivalents and modifications of the present invention will be apparent to those skilled in the art, and are encompassed within the scope of the invention.

I claim:

1. A method for predicting the effect of the administration of insulin-like growth factor I (IGF-I) on serum levels of procollagen peptide (C1CP) and IGFBP-3 in a subject, comprising:

measuring the subject's serum level of thyroid stimulating hormone ("[TSH]");

measuring the subject's serum level of total tetraiodothyronine ("[tT4]");

measuring the subject's serum level of IGF-I ("[IGF-I]"); and calculating said subject's responsiveness by the formula $$P = \frac{\log([TSH] + 1.) \times [tT4]}{[IGF - I]}$$

wherein P is the subject's responsiveness, [TSH] is the basal concentration of TSH in micro international units per milliliter of serum ($\mu$IU/mL), [tT4] is the basal concentration of total T4 in nanograms per milliliter of serum (ng/mL), and [IGF-I] is the basal concentration of IGF-I in ng/mL.

2. A method for predicting the effect of the administration of insulin-like growth factor I (IGF-I) on serum levels of procollagen peptide (C1CP) in a subject, comprising:

measuring the subject's serum level of thyroid stimulating hormone ("[TSH]");

measuring the subject's serum level of total tetraiodothyronine ("[tT4]");

measuring the subject's serum level of IGF-I ("[IGF-I]"); and calculating said subject's responsiveness by the formula $$P = \frac{\log([TSH] + 1.) \times [tT4]}{[IGF - I]}$$

wherein P is the subject's responsiveness, [TSH] is the basal concentration of TSH in micro international units per milliliter of serum ($\mu$IU/mL), [tT4] is the basal concentration of total T4 in nanograms per milliliter of serum (ng/mL), and [IGF-I] is the basal concentration of IGF-I in ng/mL.

3. A method for predicting the effect of the administration of insulin-like growth factor I (IGF-I) on serum levels of IGFBP-3 in a subject, comprising:

measuring the subject's serum level of thyroid stimulating hormone ("[TSH]");

measuring the subject's serum level of total tetraiodothyronine ("[tT4]");

measuring the subject's serum level of IGF-I ("[GF-I]"); and calculating said subject's responsiveness by the formula $$P = \frac{\log([TSH] + 1.) \times [tT4]}{[IGF - I]}$$

wherein P is the subject's responsiveness, [TSH] is the basal concentration of TSH in micro international units per milliliter of serum ($\mu$IU/mL), [tT4] is the basal concentration of total T4 in nanograms per milliliter of serum (ng/mL), and [IGF-I] is the basal concentration of IGF-I in ng/mL.

4. A diagnostic kit for predicting a subject's responsiveness to an insulin-like growth factor I (IGF-I) drug or treatment regiment, comprising:

at least one set of reagents for measuring biochemical parameters, resulting in at least one biochemical value; and a means for utilizing one or more biochemical values to predict the subject's responsiveness to said IGF-I drug or treatment regimen, wherein said biochemical parameters are selected from the group consisting of serum thyroid stimulating hormone (["TSH]"), total serum tetraiodothyronine ("[tT4]"), and serum IGF-I ("[IGF-I]"), and said predictive relationship is $$P = \frac{\log([TSH] + 1.) \times [tT4]}{[IGF - I]}$$

and P is said subject's responsiveness to said IGF-I drug or treatment regimen.

5. The diagnostic kit of claim 4 wherein said IGF-I drug or treatment regimen is parenteral administration of IGF-I.

6. The diagnostic kit of claim 5 wherein said IGF-I drug or treatment regimen is administration of IGF-I combined with insulin-like growth factor binding protein 3 (IGFBP-3).

* * * * *

UNITED STATES PATENT AND TRADEMARK OFFICE

CERTIFICATE OF CORRECTION

PATENT NO. : 5,824,467

DATED : October 20, 1998

INVENTOR(S) : D. Mascarenhas

It is certified that error appears in the above-identified patent and that said Letters Patent is hereby corrected as shown below:

At column 10, line 3, immediately after "[", delete "GF-I" and insert --IGF-I--.

Signed and Sealed this

Second Day of February, 1999

Attest:

Attesting Officer

Acting Commissioner of Patents and Trademarks